United States Patent [19]

Nishimura et al.

[11] 3,987,071

[45] Oct. 19, 1976

[54] METHOD FOR REFINING 11-CYANO-UNDECANOIC ACID

[75] Inventors: Kenji Nishimura; Shinichi Furusaki; Kazuo Kuniyoshi, all of Ube, Japan

[73] Assignee: UBE Industries, Ltd., Ube, Japan

[22] Filed: Jan. 23, 1975

[21] Appl. No.: 543,446

[30] Foreign Application Priority Data

Feb. 5, 1974  Japan.................................. 49-14103

[52] U.S. Cl.............................. 260/404.5; 260/404
[51] Int. Cl.².......................................... C07C 101/04
[58] Field of Search........................ 260/404, 404.5

[56] References Cited
UNITED STATES PATENTS 2,862,940  12/1958  Otsuki et al. ....................... 260/404
3,217,027  11/1965  Little .............................. 260/404 X

FOREIGN PATENTS OR APPLICATIONS 894,720  4/1962  United Kingdom................. 260/404

*Primary Examiner*—Patrick P. Garvin

[57] ABSTRACT

A crude 11-cyano-undecanoic acid in the form of the free acid or its ammonium salt is refined by bringing a refining gas containing ozone therein into contact with a solution of the crude 11-cyano-undecanoic acid or its ammonium salt in a substantially anhydrous organic solvent which is non-reactive with the ozone at a temperature of 0° to 100° C, for example, formic acid, acetic acid, propionic acid, chloroform, tetrachloromethane, dichloroethane or trichloroethane.

9 Claims, No Drawings

METHOD FOR REFINING 11-CYANO-UNDECANOIC ACID

The present invention relates to a method for refining 11-cyano-undecanoic acid, and more particularly, relates to a method for refining 11-cyano-undecanoic acid from a crude 11-cyano-undecanoic acid containing colored substances as impurities.

11-cyano-undecanoic acid is useful as an intermediate material for producing polymeric materials. For example, 11-cyano-undecanoic acid is converted to 12-amino-dodecanoic acid by hydrogenation. The 12-amino-dodecanoic acid is polymerized to produce Nylon 12.

British Pat. No. 1,198,422 discloses a method for producing 11-cyano-undecanoic acid by thermally decomposing 1, 1'-peroxy-dicyclohexylamine at a high temperature of 300° to 1000° C. German Pat. application Laying-open No. 2,038,956 discloses an improved method for producing 11-cyano-undecanoic acid by the introduction of an inert gas into the decomposition system.

The crude oily material obtained by those methods contains besides 11-cyano-undecanoic acid in an amount corresponding to 50 to 60% of the weight of the 1, 1'-peroxydicyclohexylamine, ε-caprolactam in an amount corresponding to 10 to 20% thereof, cyclohexanone in an amount corresponding to 10 to 20% thereof and other by-products (including saturated and unsaturated carboxylic acids, nitriles and cyclic imides) in an amount corresponding to 10 to 20% thereof. Generally, the crude oily material is dark brown or brownish black. Accordingly, in order to obtain 11-cyano-undecanoic acid usable as a material for the chemical industry, it is required that 11-cyano-undecanoic acid having impurities and coloring substances in an amount as small as possible be isolated with a high recovery yield from the crude oily material.

For recovering 11-cyano-undecanoic acid from the crude oil it may be subjected to distillation. However, since 11-cyano-undecanoic acid has low volatility and poor thermal stability, a substantial amount of 11-cyano-undecanoic acid is inevitably decomposed during the distillation period. This results in a low recovery yield of 11-cyano-undecanoic acid. Further, since the crude material contains impurities having a boiling point close to that of 11-cyano-undecanoic acid, it is difficult to obtain high purity 11-cyano-undecanoic acid.

British Pat. No. 1,289,680 discloses a method for isolating refined 11-cyano-undecanoic acid in the form of solid particles by spraying a crude 11-cyano-undecanoic acid which has been melted or dissolved in a solvent miscible with water, into water or water containing the solvent. According to the British Patent method, 11-cyano-undecanoic acid can be recovered quantitatively from the crude oily material. However, the British Patent method has a disadvantage in that the refined 11-cyano-undecanoic acid still contains a relatively large amount of impurities, particularly, coloring substances.

British Pat. No. 1,266,213 discloses a method for isolating 11-cyano-undecanoic acid by dissolving the crude oily material in a solvent containing ammonia, crystallizing the ammonium salt of 11-cyano-undecanoic acid by cooling and, then, separating the crystals from the mother liquid containing impurities. This method can recover 11-cyano-undecanoic acid having a relatively high purity. However, this yield is not sufficiently high.

In U.S. patent application Ser. No. 543,525, the inventors proposed a method for isolating 11-cyano-undecanoic acid in the form of its ammonium salt from the crude oily material by bringing ammonia gas into contact with a solution of the crude oily material in a solvent consisting an aromatic hydrocarbon having 6 to 8 carbon atoms, and then separating the crystallized ammonium salt from the solution. However, complete elimination of colored impurities is still difficult.

Accordingly, in order to obtain high purity colorless 11-cyano-undecanoic acid or its ammonium salt directly usable in the chemical industry, it is required that the 11-cyano-undecanoic acid or its ammonium salt isolated by the conventional methods described hereinbefore be further purified by way of recrystallizations repeated twice or more. However, the repeated recrystallizations result in operational complexity and in economical disadvantages.

The object of the present invention is to provide a method for refining 11-cyano-undecanoic acid in the form of free acid or its ammonium salt by a simple and easy operation in order to obtain high purity colorless 11-cyano-undecanoic acid.

The above-stated object can be accomplished by the method of the present invention, which comprises bringing the ozone containing gas into contact with the crude 11-cyano-undecanoic acid or its ammonia salt dissolved in an inert organic solvent.

The method of the present invention is based on the inventor's discovery that the colored impurities contained in the crude 11-cyano-undecanoic acid can be easily decomposed by the action of ozone, but the 11-cyano-undecanoic acid itself is quite stable against the action of ozone. This is surprising when compared with the fact that, if another oxidizing agent, for example, potassium permanganate, is used, not only colored impurities but 11-cyano-undecanoic acid itself is decomposed.

The method of the present invention can be suitably applied to a crude 11-cyano-undecanoic acid recovered from a crude oily material produced by thermally decomposing 1, 1'-peroxy-dicyclohexylamine at a temperature of 300° to 1000° C. The process of recovery is not critical to the present invention. For example, the process of the invention can be applied to said crude 11-cyano-undecanoic acid, obtained by separating the oil layer of the decomposition product, and evaporating low boilers, such as cyclohexanone, under vacuum.

However, in order to reduce wasteful consumption of ozone, it is preferable that the crude 11-cyano-undecanoic acid to be refined by the method of the present invention has a 2% solution Hazen number of at most 3,000, more preferably, at most 1,000. If the crude 11-cyano-undecanoic acid is remarkably discolored by a relatively large amount of the colored substances, it is preferable that the crude 11-cyano-undecanoic acid be preliminarily refined. The preliminary refining may be effected by way of recrystallizing the 11-cyano-undecanoic acid from a proper solvent or bringing it into contact with activated carbon. It is particularly suitable to start with the semi-refined ammonium salt of 11-cyano-undecanoic acid obtained by the inventor's process claimed in Ser. No. 543,525, wherein a crude oily material containing 11-cyano-undecanoic acid is dissolved in a solvent consisting of an aromatic hydrocarbon having 6 to 8 carbon atoms, ammonia gas is brought into contact with the solution to convert 11-cyano-undecanoic acid to its ammonium salt, which is immediately crystallized from the solution, and the crystallized ammonium salt is separated from the solution. However, crude 11-cyano-undecanoic acid or its ammonium salt recovered by other methods, for example, the methods disclosed in British Pat. Nos. 1,289,680 and 1,266,213 may also be used.

The organic solvent usable for the process of the present invention, should be non-reactive with ozone at a temperature between 0° and 100° C. Examples of such solvents are lower aliphatic carboxylic acids having 1 to 3 carbon atoms, for example, formic acid, acetic acid and propionic acid, and halogenated aliphatic hydrocarbons having 1 to 2 carbon atoms, for example, chloroform, tetrachloromethane, dichloroethane and trichloroethane. With acidic solvent, such as lower aliphatic carboxylic acids, the ammonium salt of crude 11-cyano-undecanoic acid can be directly used without converting it to free acid. But, if a halogenated aliphatic hydrocarbon is used as the solvent, the crude ammonium salt of 11-cyano-undecanoic acid should be preliminarily treated with mineral acid to convert the ammonium salt to free acid as it is insoluble in the solvent. The concentration of 11-cyano-undecanoic acid dissolved in the solvent may be varied within a wide range as long as the solution is maintained clear during the ozone treatment.

The refining gas containing ozone usable for the method of the present invention may be prepared by any of the conventional processes. Generally, the refining gas preferably contains 0.1 to 5% by volume of ozone and is prepared by feeding oxygen gas or air into an ozone generator. However, other refining gases containing ozone in a content ranging outside of the above-mentioned content range or containing ozone together with an inert gas other than air or oxygen gas, can also be utilized for the method of the present invention.

In the method of the present invention, it is preferable that the refining gas containing ozone be brought into contact with the solution of the crude 11-cyano-undecanoic acid at a temperature between 0° and 100° C, more preferably, 15° and 60° C. At a temperature higher than 100° C, the loss of ozone due to self-decomposition increases, whereas treatment below 0° C has no advantages.

To the ozone treatment, any conventional gas-liquid contacting method can be applied, although intimate contact is desirable. For example, the refining gas may be blown into the solution while the solution is stirred. In another method, the solution is brought into contact with the refining gas flowing through a bubble column or any type of gas absorber.

The ozone is preferably used in an amount of 0.05 to 5%, based on the weight of the crude 11-cyano-undecanoic acid, in response to the amount of the impurities and colored substances in the solution and contact efficiency of the refining gas with the solution. It is easily determined, by observing the color of the solution, whether or not the amount of ozone used in the refining process is sufficient. That is, the refining gas containing ozone is introduced into the solution until the solution becomes colorless. If the crude 11-cyano-undecanoic acid contains a large amount of colored substances therein and a large amount of ozone is necessary for completing the refining, it is preferable that the crude 11-cyano-undecanoic acid solution be preliminarily refined by bringing it into contact with activated carbon to remove a portion of the colored substances. However, it is one of the characteristic features of this invention that certain types of colored substances which cannot be eliminated by activated carbon, can be easily and rapidly removed from the crude 11-cyano-undecanoic acid solution by the action of ozone in accordance with the method of the present invention. Since the 11-cyano-undecanoic acid itself is stable under the refining conditions, the contact time can be varied freely.

The refined solution of the 11-cyano-undecanoic acid thus obtained may be used as a starting material for a successive process. For example, the ozone treated solution of 11-cyano-undecanoic acid in acetic acid can be subjected to hydrogenation in the presence of a noble metal catalyst to convert it to 12-aminododecanoic acid. If desired, however, refined crystals of 11-cyano-undecanoic acid can be isolated from the ozone treated solution by adopting a suitable method, for example, crystallization by cooling, precipitation by adding non-solvent for 11-cyano-undecanoic acid, such as water, cyclohexane, or petroleum ether, or by evaporating the solvent.

According to the method of the present invention the impurities and colored substances in the crude 11-cyano-undecanoic acid which cannot be eliminated by conventional refining agents, for example, activated carbon, or by conventional refining methods, for example, recrystallization from a proper solvent, can be easily and rapidly eliminated by the action of ozone, and substantially colorless high purity 11-cyano-undecanoic acid can be obtained.

The features and advantages of the present invention are further illustrated by the examples set forth below, which are not intended to limit the scope of the present invention.

In the examples, the Hazen number of the solution of 11-cyano-undecanoic acid or its ammonium salt was determined by the following method.

A standard Hazen solution was prepared by dissolving 1.246 g of potassium chloroplatinate (containing 500 mg of platinum therein) and 100 g of cobalt chloride hexahydrate into 100 ml of concentrated hydrochloric acid and adjusting the solution to a volume of 1000 ml by adding water. The standard Hazen solution has a Hazen number of 500. For example, a diluted Hazen solution which has been prepared by diluting the standard Hazen solution with water to a volume of ten times that of the original standard Hazen solution, has a Hazen number of 50. The standard Hazen solution has an absorbance of 0.674 at a wave length of 457 m$\mu$ when measured using an optical glass cell having a 5 cm thickness.

A 2% solution of 11-cyano-undecanoic acid or its ammonium salt was prepared by dissolving 2.0 g of the material to be tested in methyl alcohol and the solution was adjusted to a volume of 100 ml by adding the necessary amount of methyl alcohol.

A 25% solution of 11-cyano-undecanoic acid or its ammonium salt was prepared by dissolving 10 g of the material to be tested in acetic acid and the solution was adjusted to a volume of 40 ml by adding acetic acid.

The absorbance (As) of the solution of 11-cyano-undecanoic acid or its ammonium salt to be tested was measured by the same method as that for the standard Hazen solution. The Hazen number of the solution was determined in accordance with the following equation:

$$\text{Hazen number} = As \times \frac{500}{0.674}$$

EXAMPLE 1

A crude oily material containing 11-cyano-undecanoic acid was produced by thermally decomposing 1,1'-peroxy-dicyclohexylamine at a temperature of 500° C in accordance with the method disclosed in German Offenlegungsschrift No. 2,038,956. A semi-refined 11-cyano-undecanoic acid is recovered from said oil by dissolving the oil in toluene, introducing ammonia gas into the solution, separating the resultant ammonium salt of 11-cyano-undecanoic acid from the solution and, thereafter, converting the ammonium salt of 11-cyano-undecanoic acid to its free acid by treating it with diluted sulfuric acid at 50° C. The resultant semi-refined product had a content of 11-cyano-undecanoic acid of 98.9% by weight and a 2% solution Hazen number of 73. 70 g of the semi-refined 11-cyano-undecanoic acid was dissolved in 210 g of acetic acid. A refining gas consisting of oxygen gas containing 1.3% by volume of ozone was blown into the solution at a flow rate of 0.5 liter/minute at a temperature of 30° C while the solution was stirred. The Hazen number of the solution was decreased as indicated in Table 1.

Table 1

| Blowing time of refining gas (minutes) | 0 | 10 | 20 | 30 | 40 | 60 |
|---|---|---|---|---|---|---|
| Hazen number of refined solution | 908 | 557 | 171 | 125 | 111 | 93 |

After the 60 minutes blowing of the ozone-containing oxygen, 45 parts by weight of the solution were mixed with 55 parts by weight of water and heated to a temperature of 45° C to dissolve the precipitated crystals. The mixture was cooled to a temperature of 10° C to crystallize the refined 11-cyano-undecanoic acid from the mixture. The crystallized 11-cyano-undecanoic acid was filtered by means of suction, washed with 100 ml of water, and then dried. The refined colorless 11-cyano-undecanoic acid was obtained in a recovery yield of 96.0% and had a purity of 99.8% by weight and a 25% solution Hazen number of 9.

EXAMPLES 2 AND 3

In Example 2, procedures identical to those in Example 1 were repeated except that ammonium salt of crude 11-cyano-undecanoic acid was used without converting it to free acid. The refined colorless 11-cyano-undecanoic acid was obtained at a recovery yield of 96.4% and had a 25% solution Hazen number of 11 and a purity of 99.8% by weight.

In Example 3, the same procedures as in Example 2 were carried out using propionic acid as the solvent in place of acetic acid. The same results as in Example 2 were obtained.

EXAMPLE 4 AND COMPARATIVE EXAMPLE 1

From the same crude oily material as used in Example 1, a semi-refined ammonium salt of 11-cyano-undecanoic acid was prepared by crystallization from aqueous ammonia in accordance with the method of British Pat. No. 1,266,213. Said ammonium salt contained 90.5% of 11-cyano-undecanoic acid and had a 2% solution Hazen number of 140. 70 g of the semi-refined ammonium salt of 11-cyano-undecanoic acid was dissolved in 210 g of acetic acid. The solution had a Hazen number of 2,200. 2 g of activated carbon were dispersed into the solution to preliminarily remove the colored substances in the solution. The solution had a Hazen number of 1,030. The solution was brought into contact with the refining gas containing ozone in the same manner as in Example 1. The amount of the blown ozone was 1.1% based on the weight of the crude ammonium salt of 11-cyano-undecanoic acid. 45 parts by weight of the refined solution were mixed with 55 parts by weight of water and the mixture was heated to a temperature of 45° C in order to completely dissolve the precipitated 11-cyano-undecanoic acid in the mixture solution. Thereafter, the mixture solution was cooled to a temperature of 10° C to allow 11-cyano-undecanoic acid to crystallize from the mixture solution. The crystallized 11-cyano-undecanoic acid was filtered by means of suction, and washed with 100 ml of water, and then dried. The refined 11-cyano-undecanoic acid was obtained in a recovery yield of 98.0% and had a purity of 99.8% by weight and a 25% solution Hazen number of 10.

In Comparative Example 1, the exact same procedures as in Example 4 were repeated except that the ozone-treatment was omitted. The resultant crystallized 11-cyano-undecanoic acid had a 25% solution Hazen number of 158. The substantial improvement of Hazen number was not achieved even when an increased amount of activated carbon was added.

EXAMPLE 5

70 g of the same semi-refined 11-cyano-undecanoic acid in the form of free acid as used in Example 1 were dissolved in 210 g of 1,2-dichloroethane. The solution had a Hazen number of 980. A refining gas consisting of oxygen gas containing 1.3% by volume of ozone was blown into the solution at a flow rate of 0.5 liters/minute at a temperature of 30° C for 50 minutes while the solution was stirred. After the complete blowing of the refining gas, the solution contained a very small amount of suspended substance. The solution was filtered. The filtered solution had a Hazen number of 78. The solution was subjected to evaporation to dryness. Refined 11-cyano-undecanoic acid was obtained quantitatively and had a 25% solution Hazen number of 32 and a purity of 99.2% by weight.

EXAMPLE 6

60 g of the same semi-refined 11-cyano-undecanoic acid in the form of free acid as used in Example 1 were dissolved in 360 g of tetrachloromethane at a temperature of 45° C. The solution had a Hazen number of 830. A refining gas consisting of oxygen gas containing 1.3% by volume of ozone was blown into the solution at a flow rate of 0.5 liters/minute at a temperature of 45° C for 50 minutes. In order to remove a small amount of suspended substance, the solution was filtered and then subjected to the measurement of Hazen number. The Hazen number was 30. The solution was cooled to a temperature of 10° C in order to crystallize the refined 11-cyano-undecanoic acid from the solution. The crystalline colorless 11-cyano-undecanoic acid was obtained in a recovery yield of 93.5% and had a 25% solution Hazen number of 30 and a purity of 99.2% by weight.

EXAMPLE 7

A solution was prepared by dissolving 70 g of the same semi-refined 11-cyano-undecanoic acid in the form of free acid as used in Example 1 in 210 g of chloroform. The solution had a Hazen number of 1250. A refining gas consisting of 1.3% by volume of ozone and the balance consisting of oxygen was blown into the solution at a flow rate of 0.5 liters/minute at a temperature of 30° C for 60 minutes while the solution was stirred. After the suspended substance in the filtrate was removed by filtration, the solution had a Hazen number of 190. The chloroform was evaporated from the filtrate and refined colorless 11-cyano-undecanoic acid was recovered as residue. The crystallized colorless 11-cyano-undecanoic acid was obtained in a quantitative recovery yield, which had a purity of 99.2% by weight and a 25% solution Hazen number of 53.

What we claim is:

1. A method for refining 11-cyano-undecanoic acid, comprising dissolving a crude 11-cyano-undecanoic acid in the form of free acid or ammonium salt in an organic solvent consisting of at least one organic compound selected from the group consisting of aliphatic carboxylic acids having 1 to 3 carbon atoms and halogenated aliphatic hydrocarbons having 1 to 2 carbon atoms, and bringing a refining gas containing 0.1 to 5% by volume of ozone therein into contact with the crude 11-cyano-undecanoic acid solution at a temperature of 0° to 100° C.

2. A method as set forth in claim 1, wherein said crude 11-cyano-undecanoic acid in the form of free acid or its ammonium salt is recovered from a crude oily material which has been prepared by thermally cracking 1, 1′-peroxy-dicyclohexylamine at a temperature of 300° to 1000° C.

3. A method as set forth in claim 1, wherein said aliphatic carboxylic acid is selected from the group consisting of formic acid, acetic acid and propionic acid.

4. A method as set forth in claim 1, wherein said halogenated aliphatic hydrocarbon is selected from the group consisting of chloroform, tetra-chloromethane, dichloroethane and trichloroethane.

5. A method as set forth in claim 1, wherein said 11-cyano-undecanoic acid in the form of its ammonium salt is dissolved in a solvent consisting of an aliphatic carboxylic acid having 1 to 3 carbon atoms.

6. A method as set forth in claim 1, wherein said contacting temperature is between 15° and 60° C.

7. A method as set forth in claim 1, wherein said ozone is used in an amount of 0.05 to 5% based on the weight of said crude 11-cyano-undecanoic acid.

8. A method as set forth in claim 1, wherein said organic solvent solution is brought into contact with activated carbon to preliminarily refine it.

9. A method as set forth in claim 1, further comprising isolating said refined 11-cyano-undecanoic acid in the form of free acid or its ammonium salt from said organic solvent solution by way of crystallizing it from the solution.

* * * * *